US008367109B2

(12) United States Patent
Chidambaram et al.

(10) Patent No.: US 8,367,109 B2
(45) Date of Patent: Feb. 5, 2013

(54) MICROBES ENCAPSULATED WITHIN CROSSLINKABLE POLYMERS

(75) Inventors: Devicharan Chidambaram, Middle Island, NY (US); Ying Liu, Stony Brook, NY (US); Miriam H. Rafailovich, Plainview, NY (US)

(73) Assignees: Brookhaven Science Associates, LLC, Upton, NY (US); The Research Foundation of State University of New York, Stony Brook, NY (US)

( * ) Notice: Subject to any disclaimer, the term of this patent is extended or adjusted under 35 U.S.C. 154(b) by 530 days.

(21) Appl. No.: 12/420,088

(22) Filed: Apr. 8, 2009

(65) Prior Publication Data

US 2009/0258051 A1 Oct. 15, 2009

Related U.S. Application Data

(60) Provisional application No. 61/043,516, filed on Apr. 9, 2008.

(51) Int. Cl.
*A61K 9/14* (2006.01)
(52) U.S. Cl. ........................................................ 424/486
(58) Field of Classification Search .................... 424/486
See application file for complete search history.

(56) References Cited

U.S. PATENT DOCUMENTS

| 4,518,693 | A | * | 5/1985 | Kuu | 435/178 |
| 6,131,341 | A | * | 10/2000 | Wade et al. | 49/478.1 |
| 6,376,210 | B1 | * | 4/2002 | Yuan | 435/18 |
| 7,172,765 | B2 | | 2/2007 | Chu et al. | |
| 2006/0257995 | A1 | * | 11/2006 | Simpson et al. | 435/287.2 |

FOREIGN PATENT DOCUMENTS

WO WO 9637519 A1 * 11/1996
WO WO 2007095335 A2 * 8/2007

OTHER PUBLICATIONS

Renneberg et al (Journal Applied Microbiology and Biotechnology 21 (Nos. 3-4):180-181 (Feb. 1985)).*
Cohn, D., Sosnik, A., Garty, S., "Smart Hydrogels for in Situ Generated Implants". Biomacromolecules, 6: 1168-1175 (2005).
Gensheimer, M., Becker, M., Brandis-Heep, A., et al., "Novel Biohybrid Materials by Electrospinning: Nanofibers of Poly(ethylene oxide) and Living Bacteria", Advanced Materials, 19: 2480-2482 (2007).
Ji, Y., Li, B., Ge, S., et al., "Structure and nanomechanical characterization of electrospun PS/clay nanocomposite fibers", Langmuir, 22: 1321-1328 (2006).
Salalha, W., Kuhn, J., Dror, Y., et al., "Encapsulation of bacteria and viruses in electrospun nanofibres", Nanotechnology, 17: 4675-4681 (2006).

* cited by examiner

*Primary Examiner* — Benjamin Packard
(74) *Attorney, Agent, or Firm* — Hoffmann & Baron, LLP

(57) ABSTRACT

The invention relates to porous films comprising crosslinked electrospun hydrogel fibers. Viable microbes are encapsulated within the crosslinked electrospun hydrogel fibers. The crosslinked electrospun hydrogel fibers are water insoluble and permeable. The invention also relates to methods of making and using such porous films.

39 Claims, 16 Drawing Sheets

| Sample ID | Storage temperature in Celsius | Days in storage | Ethanol concentration (vol %) |
|---|---|---|---|
| | | | |
| | | | |
| Sterile Media | | | 0.00 |
| Control - ZM | | | 0.92 |
| Electrospun Samples | | | |
| Electrospun ZM | Added to media immediately | | 0.69 |
| Electrospun ZM | 4 | 1 | 0.58 |
| Electrospun ZM | 4 | 3 | 0.62 |
| Electrospun ZM | 4 | 7 | 0.79 |
| Electrospun ZM | -70 | 31 | 0.82 |
| Electrospun ZM | -70 | 60 | 0.52 |

Figure 16

MICROBES ENCAPSULATED WITHIN CROSSLINKABLE POLYMERS

CROSS-REFERENCE TO RELATED APPLICATION

This application claims the benefit of U.S. Provisional Application No. 61/043,516, filed Apr. 9, 2008, which is incorporated herein by reference in its entirety.

This invention was made with Government support under contract number DE-AC02-98CH10886, awarded by the U.S. Department of Energy. The Government has certain rights in the invention.

BACKGROUND OF THE INVENTION

Electrospinning is an atomization process whereby the interactions between an electrostatic field and a fluid are exploited to form nanoscale and microscale polymer fibers. These fibers can be collected as an interconnected web containing relatively thin fibers. Porous films resulting from these fibers have very large surface area to volume ratios, high permeability and small pore size that make them appropriate for a wide range of applications. Therefore these films are considered to be an ideal media to fix or encapsulate bacteria.

Earlier attempts to encapsulate microbes in nanofibers have been made by electrospinning various polymers. See for example, Salalha et al., *Nanotechnology* 17, 4675-4681 (2006); and Gensheimer et al., *Advanced Materials* 19, 2480-2482 (2007).

The previous attempts typically involved bulk immobilization in gels. Either the microbe did not survive or if it did the thick bulk polymer lacked porosity and was not easy to work with due to its thickness. When encapsulation via electrospinning was attempted, either, the microbe did not survive the process of encapsulation; or, if the microbe did survive, the final material was soluble in aqueous solution. A water soluble biohybrid material has minimal use since an aqueous environment would lead to disintegration of the material, thereby releasing the microbes. Therefore, these previous attempts to create useful encapsulated microbes produced materials having little practical value.

Thus there is a need for a process whereby bio-hybrid/biofunctional materials encapsulating microbes can be reliably formed while preserving the viability of the microbes, and wherein the final material is insoluble in aqueous solution.

SUMMARY OF THE INVENTION

In one embodiment, the invention relates to a porous film comprising crosslinked electrospun hydrogel fibers. The crosslinked electrospun hydrogel fibers are water insoluble and permeable Viable microbes are encapsulated within the crosslinked electrospun hydrogel fibers.

In another embodiment, the invention relates to a method of encapsulating microbes within a polymer. The method comprises (a) providing a mixture of microbes and a polymer, wherein the polymer is capable of forming a hydrogel, is water soluble, and is crosslinkable; (b) electrospinning the polymer to form electrospun fibers, wherein the microbes are encapsulated within the electrospun fibers; and (c) crosslinking the electrospun fibers to form electrospun hydrogel fibers that are water insoluble and permeable. The fibers contain viable microbes therein.

In a third embodiment, the invention relates to a method of crosslinking electrospun fibers comprising microbes encapsulated within the electrospun fibers. In the method, the electrospun fibers are crosslinked in a liquid polyol. After crosslinking, the electrospun fibers form a hydrogel that is insoluble and permeable, and that encapsulates viable microbes.

In a fourth embodiment, the invention relates to a method for removing pollutants from an aqueous environment, the method comprising contacting the pollutants with a porous film that comprises crosslinked electrospun hydrogel fibers. Microbes are encapsulated within the crosslinked electrospun hydrogel fibers. The crosslinked electrospun hydrogel fibers are water insoluble and permeable, and encapsulate microbes that are viable and capable of bioremediation.

In a fifth embodiment, the invention relates to a biosensor comprising microbes encapsulated within crosslinked electrospun hydrogel fibers. Encapsulated microbes are viable and capable of generating a signal in response to a chemical compound. The crosslinked electrospun hydrogel fibers are water insoluble and permeable.

In a sixth embodiment, the invention relates to a method of regenerating healthy bioflora. The method comprises implanting into the gastrointestinal tract of patients in need thereof a porous film that comprises crosslinked electrospun hydrogel fibers. Microbes that are viable and capable of regenerating healthy bioflora in the gastrointestinal tract of the patient are encapsulated within the fibers. The crosslinked electrospun hydrogel fibers are water insoluble and permeable.

In a seventh embodiment, the invention relates to an electrode comprising microbes encapsulated within crosslinked electrospun hydrogel fibers. The encapsulated microbes are viable and are capable of electron generation or utilization. Such electrodes are useful, for example, in microbial fuel cells and waste water treatment. The crosslinked electrospun hydrogel fibers are water insoluble and permeable.

BRIEF DESCRIPTION OF THE DRAWINGS

FIG. 16: Amount of ethanol produced by Z. mobilis after inoculation of the sterile medium (composition provided in methods section) with various pre- and post electrospun microbial samples. The amount of ethanol produced by the electrospun samples (immediately and after storage) is slightly lower than that produced by the control (free culture, pre-electrospinning). This could be explained via the longer lag phase growth experienced by the electrospun samples, thereby providing more aeration and leading to lower ethanol production.

DETAILED DESCRIPTION OF THE INVENTION

Figure 1:
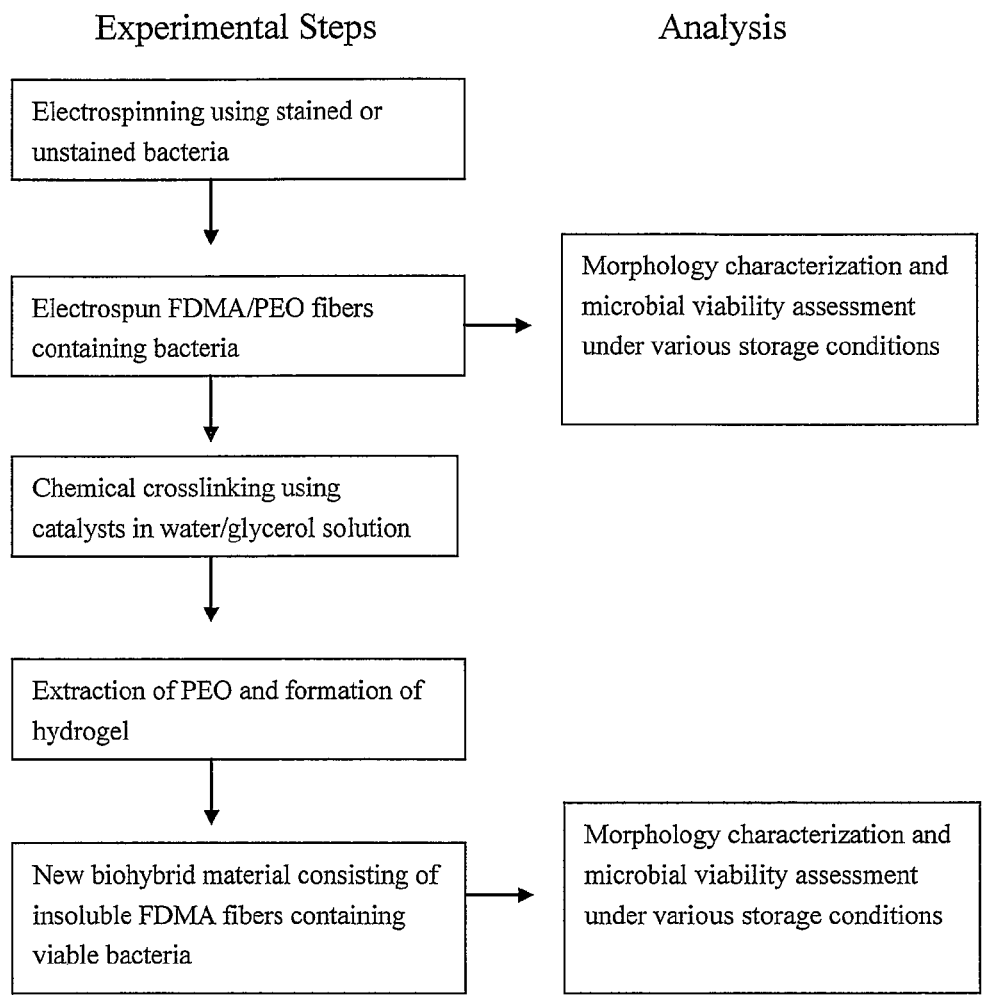
FIG. 1. A schematic describing the different stages of the process that were undertaken to generate the biohybrid material. Further, the chart shows the various stages at which the fibers were characterized and analyzed.

The present invention is based on the discovery of a method to crosslink electrospun polymeric fibers that encapsulate microbes so that (i) the fibers are permeable to, and insoluble in, water, and (ii) the fibers encapsulate viable microbes therein. The invention includes crosslinked polymeric porous films made from such microbe-encapsulating fibers, and methods of making and using such films such that moisture is available to the microbes, even though the fibers and films are water insoluble. The films of the invention are usefully thought of as artificial biofilms.

Methods of Making the Crosslinkable Polymers of the Invention

Polymers

In one aspect, the invention relates to methods of encapsulating microbes within the fiber structure of a polymer. The polymer used in the methods of the invention is any polymer that is water soluble, and is crosslinkable. Such polymers are well known in the art.

The polymer must also be capable of forming a hydrogel after being electrospun and crosslinked. A hydrogel is a network of polymer chains that is water-insoluble and is super absorbent (e.g., the hydrogel can contain more than 99% water). Hydrogels also possess a high degree of flexibility very similar to natural tissue, due to their significant water content.

Some examples of suitable polymers include glycosaminoglycans and proteins. Preferred polymers, however, are polyethers. The polymers can be used by themselves, or as copolymers, as well as mixtures of polymers and copolymers.

Some examples of suitable polyethers include polyethylene oxide, polypropylene oxide, mixtures thereof, and co-polymers thereof. The molecular weight of the polymer, e.g., polyethylene oxide or polypropylene oxide, is not critical as long as the polymer can be electrospun, e.g., is soluble; can be, or is modified to be, crosslinkable, and can form a hydrogel upon being crosslinked. For example, the molecular weight can be as low as about 1,000, more typically as low as about 3,000, and even more typically as low as about 6,000. The molecular weight can be as high as about 1,000,000, more typically as high as about 80,000, and even more typically as high as about 60,000.

It should be noted that poly(ethylene oxide) (PEO) generally refers to higher molecular mass polymers, e.g., a molecular mass above 9,000 g/mol, and sometimes above 20,000 g/mol. Poly(ethylene glycol) (PEG) generally refers to oligomers and lower molecular mass polymers, e.g., a molecular mass below 9,000 g/mol, and sometimes below 20,000 g/mol. Polyoxyethylene (POE) generally refers to a polymer of any molecular mass. In this specification, the terms polyethylene oxide and poly(ethylene oxide) (PEO) are used interchangeably to mean any of the above polymers having the molecular weight provided.

An example of a polyether copolymer is a polyethylene oxide-polypropylene oxide terpolymer or triblock copolymer. A suitable triblock copolymer of polyethylene oxide-polypropylene oxide is $PEO_{99}$-$PPO_{67}$-$PEO_{99}$ DMA (FDMA), which has the same characteristics of, and is available as, Pluronic® F127 from BASF Corporation.

Suitable glycosaminoglycans are also known in the art. An example of a suitable glycosaminoglycan is hyaluronic acid. The glycosaminoglycans may be modified to contain crosslinkable groups. Suitable thiol-modified hyaluronic acids include, for example, Glycosil™, Heprasil™, and Gelin-S™, all of which are available from Glycosan Biosystems.

Suitable proteins are also known in the art. A suitable protein includes collagen, preferably denatured collagen, e.g., gelatin and elastin. The protein may be modified to contain crosslinkable groups. A suitable thio-modified collagen is Gelin-S™, which is available from Glycosan Biosystems.

The polymers either contain, or are modified to contain, at least two crosslinkable functional groups. The functional groups depend on the method of crosslinking, as will be discussed below.

Some examples of suitable crosslinkable functional groups include hydroxyl groups, thiol groups, and amino groups. Other suitable crosslinkable functional groups include carbonyloxyalkyl groups, carbonylchloride groups, and carbonylbromide groups. Some examples of carbonyloxyalkyl groups include carbonyloxymethyl and carbonyloxyethyl.

Another crosslinkable functional group is a vinyl group. A vinyl group may be added to polyethylene oxide and polypropylene oxide by reaction with, for example, acryloyl chloride or methacryloyl chloride. The preparation of Pluronic® F127 having a methacrylate group at each terminus (F127-DMA) is described in Cohn, et al., Biomacromolecules, 6(3):1168-1175 (2005).

Electrospinning

A crosslinkable polymer encapsulating microbes is produced by electrospinning. The polymer contains, or is modified to contain, crosslinkable functional groups, and may be any of the polymers, described above.

In one embodiment, electrospinning is accomplished by providing a precursor mixture containing suitable microbes and a suitable crosslinkable polymer in a suitable electrospinning medium. The precursor mixture, or any part of it, may be prepared or obtained from an outside source.

The ratio of the polymer to microbes in the precursor mixture is not critical, but will affect the average number of microbes encapsulated in the electrospun fibers. For example, the ratio might be about 1 part polymer to about 2, about 6, or about 10 parts microbes.

The electrospinning of an aqueous solution of certain polymers, e.g., FDMA, into fibers may be improved by blending poly(ethylene oxide) or poly(propylene oxide) (e.g., poly (ethylene oxide) $M_w$=900 kDa, Sigma-Aldrich Inc.) with the polymer to facilitate fiber formation. The molecular weight of the polymer added to facilitate fiber formation is not critical, and may be any of the molecular weights described above for the functionalized polymer. The ratio of functionalized polymer, described above, to the poly(ethylene oxide) or poly (propylene oxide) added to improve electrospinning is higher than about 13/1, e.g., about 13/3 or 13/5. The blended poly (ethylene oxide) or poly(propylene oxide) is not crosslinked, and is optionally removed by rinsing with water, preferably deionized water.

The electrospinning medium is such that, after electrospinning, the microbes become encapsulated in the polymeric fibers, and at least a portion or all of the microbes remain viable. In addition to the microbes and polymer, the medium comprises water, preferably deionized water. Optionally, the aqueous medium further comprises other solvents that can be electrospun, and that do not harm the microbes, for example, with respect to their function and/or viability. Other solvents include, for example, glycerol and sugar alcohols. Some suitable sugar alcohols include, for example, xylitol, mannitol and lactitol. Some examples of precursor mixtures comprise a suitable microbe and a suitable polymer in an aqueous medium, a sol-gel or particulate suspension of the polymer.

The precursor mixture comprising the polymer and the microbes is then electrospun. Electrospinning is well known in the art. See, for example, Chu et al., U.S. Pat. No. 7,172,765 and Li et al., *Advanced Materials* 16(14), 1151-1170 (2004).

An example of an apparatus for producing the electrospun hydrogel fibers of the invention, which uses a multiple jet electrospinning system, is shown schematically in FIG. 11. Referring to FIG. 11, the precursor mixture is supplied by a micro-flow pump system 1. The pump system 1 is operatively connected to a computer 2 which controls the flow rate of the precursor mixture to selected spinnerets by controlling pressure or flow rate See, for example, Ji et al., Langmuir 22:1321-1328 (2006).

The diameters of the fibers can be controlled by varying the parameters of electrospinning. For example, varying the flow rate of the precursor mixture affects the diameter of the hydrogel fibers. Typically, the fibers are about 0.2 to about 20 microns in diameter, more typically the fibers are about 0.6 to about 5 microns in diameter.

Preferably, the diameter of the electrospun fibers is just large enough to fully encapsulate microbes within the fiber structure. Microbes have various sizes. For example, microbes typically vary in size from about 0.5 to about 4.0 microns; although other microbes may be as small as about 0.1 to about 0.2 microns. The optimized process conditions lead to fibers being only slightly larger (e.g., about 50%, preferably about 10% larger) than the average size of the microbes being encapsulated, thereby encapsulating the microbes with only a thin layer of polymeric material.

The electrospinning process results in the fibers forming a permeable film with an open pore structure. These films have very large surface area to volume ratios. Prior to crosslinking, the fibers are soluble in water.

The parameters of electrospinning can be varied to obtain films of a certain morphology. For example, the flow rate or collection time of the precursor mixture can be varied to control film thickness, pore size, and film density.

Crosslinking

The electrospun fibers are crosslinked to render them water insoluble and to form a hydrogel. Crosslinking is achieved by contacting the fibers with a crosslinking agent in a liquid polyol. Examples of suitable liquid polyols include glycerol and sugar alcohols. Some suitable sugar alcohols include, for example, xylitol, mannitol and lactitol. In some embodiments, up to about 70% of the liquid polyol by volume is replaced with water, preferably up to about 50% of the liquid polyol by volume is replaced with water, most preferably up to about 30% of the liquid polyol by volume is replaced with water.

In one embodiment wherein the polymer contains vinyl groups, the crosslinking agent is a redox system that produces a free radical initiator. Suitable redox systems are known in the art. For example, a suitable redox system comprises a persulfate salt, e.g., ammonium persulfate, and a metabisulfite salt, e.g., sodium metabisulfite. Another suitable redox system comprises a persulfate salt, e.g., ammonium persulfate, and a combination of a ferrous salt, e.g., ferrous sulfate, and a vinylic carboxylic acid, e.g., ascorbic acid. A preferred redox system comprises ammonium persulfate and a combination of ferrous sulfate and ascorbic acid.

The electrospun fibers are contacted with the crosslinking agent under conditions that allow crosslinking to occur at a reasonable rate, that do not degrade the electrospun fibers, and that are not harmful to the microbes. For example, the crosslinking may be carried out overnight with ammonium persulfate, ferrous sulfate and ascorbic acid at about room temperature in glycerol/water 70/30 by volume.

In another embodiment, the crosslinking agent comprises a crosslinker molecule. Crosslinker molecules comprise at least two functional groups, preferably two terminal functional groups.

The functional groups of the crosslinker molecule react with the crosslinkable groups of the polymer. For example, if the polymer has carbonyloxyalkyl groups (—C(═O)OR), carbonylchloride groups (—C(═O)Cl), or carbonylbromide groups (—C(═O)Br), the crosslinker molecule might have hydroxyl groups, amino groups, or thiol groups. Alternatively, if the polymer has hydroxyl groups, amino groups, or thiol groups, the crosslinker molecule might have carbonyloxyalkyl groups, carbonylchloride groups, or carbonylbromide groups. Examples of carbonyloxyalkyl groups include carbonyloxymethyl and carbonyloxyacrylethyl.

Preferably, the two functional groups of a crosslinker molecule are separated by an alkyl chain. The minimum number of atoms in these alkyl chains is two. The maximum number of atoms in these alkyl chains is about 300, preferably about 275, and most preferably about 250. Preferably, the crosslinker molecule has one heteroatom (e.g., O, S, NH) separating at least some of the pairs of carbon atoms in the chain. Preferably, the crosslinker molecule has one heteroatom (e.g., O, S, NH) separating all of the pairs of carbon atoms in the chain.

In another embodiment, the crosslinker molecule is formaldehyde. Formaldehyde crosslinks through a —CH$_2$— linkage. See, for example, Solomon et al., PNAS 82, 6470-6475 (Oct. 1, 1985).

The crosslinked electrospun polymeric materials of the invention are in the form of hydrogel fibers that are water insoluble and permeable, and have viable microbes encapsulated within the fiber structure. The fibers form a film during the electrospinning process. The insoluble nature of the material is evidence of crosslinking.

The films have a high permeability and a large surface area. Additionally, the films have an open pore structure. The size of the pores are such that water molecules are able to enter the interior of the films, and come into contact the encapsulated microbes. The porosity of the films depends, at least in part, on the density of the fibers. Accordingly, the films can be made more porous by increasing rate and time of the electrospinning process, as described above.

Films of the invention can have any thickness suitable for a particular end use. For example, the thickness can range from about 0.5 micron to about 10 cm; more typically, from about 5 to about 10,000 microns; and most typically, from about 10 to about 5000 microns.

The properties of the films can be adjusted by varying several parameters, such as, for example, the specific polymer composition, fiber diameter, film morphology, molecular weight distribution, and film porosity. For example, the film can contain fibers having different microbes, or different concentrations of microbes, to form a composite of different fibers.

In one embodiment, the film can contain multiple layers. The layers can have the same or different polymer/microbe compositions, fiber diameters, film morphologies and film porosities. Multi-layered films offer yet another way to control properties of the films. In one embodiment, microbes can be incorporated between the layers of the multi-layered films in addition to incorporating the microbes into the fiber structures themselves.

The films can be shaped into a variety of useful articles depending upon their end use or application. For example, the articles can be in the shape of a tube, rod, plug, block, etc.

Microbes

Any useful microbe that a portion or all of which remains viable after encapsulation within a polymer fiber can be used in the invention. Microbes include any naturally-occurring or genetically-engineered, single cell or multiple cell submicroscopic organism. Some examples of microbes include bacteria, fungi, archaea, protists, and algae. In this specification, microbes also include yeast and viruses.

Typically, at least some of the microbes encapsulated in the fibers remain viable with the exclusion of light at 4° C. for at least up to seven days; and at −70° C. for at least up to two months. Examples of useful microbes include those that can be used in environmental, medical, energy generation and biosensor applications. The microbes used in a particular article depend on their end use or application.

For example, films comprising alkane-utilizing bacteria can be used in bioremediation to destroy, or reduce the concentration of, hazardous wastes. For instance, these films can be used to clean up contaminated sites such as waterways, soils, sludges, and waste streams; and to clean up chemical spills, leaking underground storage gasoline tanks, and toxic industrial effluents.

Some examples of suitable alkane-utilizing bacteria include *Pseudomonas, Variovorax, Nocardia, Chryseobacterium, Comamonas, Acidovorax, Rhodococcus, Aureobacterium, Micrococcus, Aeromonas, Stenotrophomonas, Sphingobacterium, Shewanella, Phyllobacterium, Clavibacter, Alcaligenes, Gordona, Corynebacterium, Cytophaga Mycobacterium* and *Nocardia*. Examples of some suitable bacterial species include *Pseudomonas rubrisubalbicans, Pseudomonas aeruginosa, Pseudomonas putida, Pseudomonas oleovorans, Variovorax paradoxus, Nocardia asteroides, Nocardia restricta, Chryseobacterium indologenes, Comamonas acidovorans, Acidovorax delafieldii, Rhodococcus rhodochrous, Rhodococcus erytlropolis, Aureobacterium esteroaromaticum, Aureobacterium saperdae, Micrococcus varians, Micrococcus kristinae, Aeromonas caviae, Stenotrophomonas maltophilia, Sphingobacterium thalpophilum, Clavibacter michiganense, Alcaligenes xylosoxydans, Corynebacterium aquaticum* B and *Cytophaga johnsonae*. Additionally, *Clostridium* is also useful for remediating organic compounds such as biphenyls, chlorinated organics, etc.

Microbes known for their ability in remediation of hazardous metals and radioactive wastes can also be used in the films. Examples of such microbes include members of the genus *Clostridium* (anaerobic), *Shewanella* (facultative) and *Pseudomonas* (aerobic), which can be used to remediate metals such as lead, arsenic, cadmium, mercury, chromium, nickel and zinc; as well as radionuclides such as uranium, plutonium, technetium, etc.

Hyper-metal-accumulating microbes, such as members of the genus *Cupriavidus, Ralstonia*, and *Pseudomonas* (aerobic), are additional examples of useful microbes. These microbes accumulate metals such as zinc, nickel, manganese and cadmium, thereby removing them from the environment. Films containing these microbes can be used as a permeable reactor barrier for remediation of contaminated underground water. Such reactors can be removed periodically and the waste removed as solid waste.

As a medical application, porous films of the invention are formed into articles suitable for implanting into the intestinal tracts of patients. Suitable articles include, for example, scaffolds or patches. The articles contain microbes that restore healthy bioflora, and are implanted into the gastrointestinal tract of patients in need thereof, e.g., patients whose stomach and/or intestinal bioflora are destroyed by, for example, radiation exposure or large doses of antibiotics. The implanted articles regenerate healthy bioflora.

Examples of microbes useful for restoration of healthy bioflora (i.e., probiotic microbes) include strains of the genera *Lactobacillus* and *Bifidobacterium*. Some examples of species include *Lactobacillus acidophilus, Lactobacillus casei, Lactobacillus bulgaricus* and *Streptococcus thermophilus*. An example of probiotic yeast is *Saccharomyces boulardii*.

The films of the present invention have useful applications in the energy fields. For example, the films can be used as electrode materials in bio-film reactors, biofuel cells, microbial fuel cells and fermentation reactors. In such applications, the polymer may be electrospun with carbon powder or other conducting material. For example, a bio-film reactor, may use porous films comprising microbes encapsulated within crosslinked electrospun hydrogel fibers. Encapsulated microbes are viable and are capable of producing metabolites. Such reactors are useful, for example, in production of metabolites like ethanol and pharmaceutical products.

An example of a bacterium that is useful in biofuel applications is *Zymomonas* sp. An example of a species is *Zymomonas mobilis*. *Zymomonas* has a very high ethanol yield from glucose, no oxygen requirement (thus negating the need for expensive oxygen transfer), and high ethanol tolerance. Genetically-engineered *Escherichia coli* have also been found to be useful as a biofuel synthesizer. See, for example, Kalscheuer et al., Microbiology 152:2529-2536 (2006); and Qureshi, N. et al., Institution of Chemical Engineers Transactions. 84(2): 114-122 (2006). Another useful microbe in biofuel applications is *Saccharomyces cerevisiae*.

The films of the present invention can also be used as biosensors. The microbe functions as the sensing element which then provides an electronic signal. The signal can be amplified and transduced to a current signal or a voltage signal. For instance, a biosensor can have a source terminal and a drain terminal connected to the film. The biosensor can further be linked to a detector capable of measuring a current-voltage characteristic of the film, and/or linked to an electrical/electronic device (e.g., light bulb or a liquid crystal display (LCD)).

Examples of bacteria that are useful in the biosensors of the invention include members of genus *Bacillus*, such as *Bacillus Subtilus*, for the determination of the presence of aspartame (organic). See, for example, Journal Applied Microbiology and Biotechnology 21 (Nos. 3-4):180-181 (February 1985). *Pseudomonas aeruginosa* and *Trichosporon cutaneum* are used in biosensors of the invention for the determination of the presence of ammonium ions. See, for example, www.ncbi.nlm.nih.gov/pubmed/1367422?dopt=Abstract.

EXAMPLES

The invention is further illustrated by the following non-limiting examples.

These examples describe the development and formation, via electrospinning, of a novel FDMA fibrous hydrogel material with encapsulated microbes. This is the first insoluble fibrous material containing viable microorganisms that has been reported. The microbes in the material were found to be viable for over a week in the dry FDMA/PEO blend scaffold at 4° C. and for over two months at −70° C. The FDMA fibers were cross-linked using a water/glycerol solvent mixture, and the APS, ferrous sulfate and AsA catalytic system. The occurrence of the crosslinking reaction was demonstrated by TG analysis. The integrity and the viability of the bacteria were maintained through the cross-linking process.

Materials and Method

Figure 15:
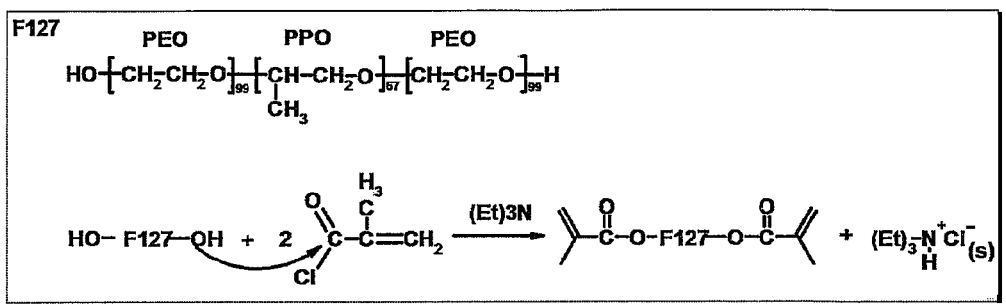
FIG. 15: Schematic showing the synthesis of F127-DMA.

Synthesis of FDMA. The synthesis and characterization of FDMA was described in Sosnik et al. *Journal of Biomaterials Science-Polymer Edition* 14(3):227-239. The chemical reaction is shown in FIG. 15. The weight average (Me) and number average molecular weight ($M_n$) of FDMA was determined using calibrated gel-permeation chromatography (GPC) to be $M_w$=21,900 Da and $M_n$=12,600 Da ($M_w/M_n$=1.3).

Bacterial Cultures. *P. fluorescens* (ATCC 55241) were cultured in a medium, 1 liter of which consisted of citric acid, 2.0 g; $MgSO_4.7H_2O$, 0.2 g; $NH_4Cl$, 1.0 g; $KH_2PO_4$, 1.0 g; $K_2HPO_4$, 1.0 g; NaCl, 5.0 g; pH 6.1 adjusted using NaOH. *Z. mobilis* (ATCC 31821) were cultured in a medium containing glucose, 20 gpl; yeast extract, 10 gpl; $KH_2PO_4$, 2 gpl and whose pH was adjusted to 6.0 using NaOH. Functionality was assessed by growing immobilized *Z. mobilis* and pure culture (control) in a fermentation medium containing glucose, 20 g; yeast extract, 10 g; $KH_2PO_4$, 2 g; and $H_2O$, 1 liter; pH=6.0. Recombinant *E. coli* bacteria expressing green fluorescent protein (GFP) was grown in Luria-Bertani (LB) medium. The cultures were grown in Erlenmeyer flasks in an incubator at 27±1° C. Typically, cultures at the end of the log phase of growth were used for electrospinning.

Fabrication of FDMA/PEO Blend Fiber. An aqueous solution of FDMA is not optimal for electrospinning into fibers, even at high concentrations. Therefore, poly(ethylene oxide) (PEO) ($M_w$=900 kDa, Sigma-Aldrich Inc.) was blended with FDMA to facilitate the fiber formation during the electrospinning process. To prepare the electrospinning solution, PEO powder was dissolved in deionized water at the following concentrations: 1 wt %, 2 wt % and 3 wt %. FDMA powder was then added into the PEO solution at a concentration of 13 wt % and allowed to dissolve for several hours at 4° C. until the solution became clear. For encapsulation experiment, pre-determined amount of the bacteria, as required, were dispersed homogenously in the FDMA/PEO solution before electrospinning. The PEO may optionally be removed by washing with water, preferably deionized water.

The experimental setup of the electrospinning stage was described in Ji et al. *Langmuir* 22(3): 1321-1328. The fibers were electrospun and collected on a sterile Si wafer for about 30 minutes to form a three-dimensional (3D) structure.

Cross-linking of the Electrospun FDMA Matrix. The catalytic system consists of ascorbic acid (AsA) (Aldrich), ferrous sulfate (Aldrich) and ammonium persulfate (APS) (Aldrich). The principle of this reaction is similar to the Fenton reaction, as reported earlier (Liang et al. *Chemosphere* 55(9): 1213-1223). APS is the free radical initiator, ferrous sulfate and AsA are used to catalyze the breakdown of the APS and, therefore, to accelerate the cross-linking reaction. This catalytic system is effective at room temperature even if the concentration of the initiator is very low. However, for the system to be highly efficient, the ratio of the APS, AsA and ferrous sulfate had to be fine tuned.

AsA, APS and ferrous sulfate solution was prepared freshly in deionized water and pre-determined amounts of those solutions were then added to the glycerol/deionized water solvent at differing glycerol:water ratios. The electrospun fibers (along with the Si wafer support) were placed into a glass vial containing 2 ml of the cross-linking solution and allowed stand overnight at room temperature. The cross-linked membrane was then washed three times with deionized water to remove unreacted monomers, and catalyst.

Finally, the membrane was soaked in deionized water for 24 hours to ensure complete extraction of the PEO and fully swell the scaffold.

Characterization of Electrospun FDMA Fiber Mats. The surface morphology of the electrospun FDMA/PEO blend fibers and FDMA fibers (with and without bacteria) were characterized using scanning electron microscopy (SEM) (LEO 1550, LEO, Germany). The swollen FDMA fibers were freeze dried (Consol 1.5, Virtis Inc. NY) at −40° C., followed by lyophilization. Samples were sputter-coated with gold for 15 seconds twice prior to SEM imaging. The fiber diameter distributions of the FDMA/PEO blend scaffolds and crosslinked FDMA scaffolds were calculated by analyzing the SEM images using Image Tool (The University of Texas Health Science Center in San Antonio) in a manner similar to that described by Boland E D et al., *Journal of Macromolecular Science-Pure and Applied Chemistry* 38(12): 1231-1243 (2001).

Thermogravimetric (TG) measurements were conducted to analyze the thermal behavior of the electrospun FDMA/PEO blend fibers, prior to and following crosslinking. TG measurements were conducted in nitrogen gas at a heating rate of 5° C./min in the temperature range between 50° C. and 500° C. using a Mettler Toledo TGA/SDTA 851 thermal analyzer. Samples with a weight of approximately 15 mg were loaded in a $SiO_2$ crucible under dry conditions.

Characterization of Microbes. The viability of the microbes was assessed using the LIVE/DEAD® BacLight™ bacterial viability kits (Molecular Probes, OR). Live microbes (intact cell membranes) stain fluorescent green, while dead microbes (damaged cell membranes) stain fluorescent red. Live and dead bacteria were later viewed simultaneously by Leica TCS SP2 laser scanning confocal microscopy (LSCM) (Leica Microsystem Inc., Bannockburn, Ill.).

The morphologies of the bacteria inside the FDMA/PEO fibers were characterized both by LSCM and SEM. For LSCM, bacteria were spun down from culture media, stained with bacterial viability kits, and then mixed with the FDMA/PEO solution, prior to electrospinning. While for GFP *E. coli*, GFP was excited at 488 nm with an argon ion laser source without any staining. For SEM studies, the bacteria were rinsed with deionized water twice, stained with 2% (w/v) uranyl acetate for 2 minutes at room temperature, spun down and mixed with the FDMA/PEO electrospinning solution. To image the bacteria inside the cross-linked FDMA fiber by SEM, the swollen fibers were freeze dried and coated with gold as described above.

Cytoxicity and Storage Evaluation. The viability of the bacteria, before and after electrospinning, was evaluated after various times of electrospinning. Bacteria containing fibers were stored under the exclusion of light at 4° C. for up to 7 days and at −70° C. for up to 2 months. Two methods were used to analyze the bacterial survival rate. The encapsulated microbes were stained with LIVE/DEAD® BacLight bacterial viability kits immediately after they were liberated from the FDMA/PEO blend fibers and then observed under LSCM. Photomicrographs of the stained bacteria were obtained. The number of bacteria alive was averaged over several views of the same condition. Bacterium counting at each time point was performed in triplicates. In the case of *Z. mobilis*, the uncross-linked fibers were dissolved in sterile bacteria culture media and/or fermentation media described earlier, whereby the immobilized microorganisms were released from the fibers. As controls, free culture and microorganisms mixed with polymeric material (prior to electrospinning) were used as inoculums. After incubation, the metabolic activity of the *Z. mobilis* was tested by analyzing the spent media for residual glucose and ethanol concentration using high performance liquid chromatography (HPLC). The cytotoxicity of the chemicals and the cross-linking process to the bacteria were also evaluated using the LIVE/DEAD® BacLight™ bacterial viability kits as explained above.

A schematic describing the different stages of the process that were undertaken in this study to generate the biohybrid material is presented in FIG. 1. Furthermore, the various stages at which the fibers were characterized and analyzed are also indicated on the schematic.

Figure 2:
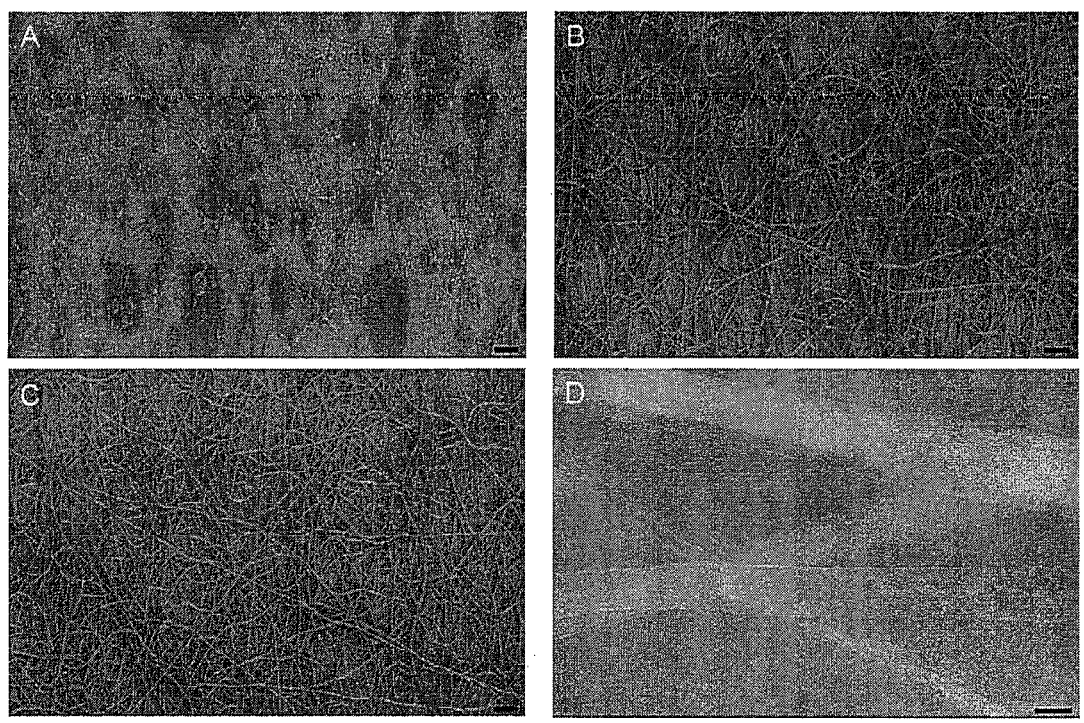
FIG. 2. SEM images of the electrospun F127-DMA/PEO blend scaffolds with different weight ratio: (A) F-DMA 13 wt %, PEO 1 wt % (13:1); (B) F-DMA 13 wt %: PEO 2 wt % (13:2); (C) and (d) F-OMA 13 wt %: PEO 3 wt % (13:3). Note (D) is the higher magnification image of the (c). Bars, 20 μm (A, B, C), 1 μm (D)

The FDMA/PEO blend solutions with different weight ratios, increasing from 13:1 to 13:3, were electrospun to fabricate fibrous membrane scaffolds as shown in FIGS. 2A-C. At an FDMA/PEO weight ratio of 13:1, very few electrospun fibers were generated and they showed a beads-on-string morphology with a high beads density. As the FDMA/PEO weight ratio increased from 13:1 to 13:3, the density of beads decreased and a uniform fibrous scaffold was obtained at an optimized weight ratio of 13:3 (FIGS. 2C and 2D), that was used in all further experiments.

The water soluble nature of FDMA presents a great challenge as any contact with water can immediately destroy the fibrous structure and therefore highly limits the application of this polymer. Cross-linking the fibers after electrospinning will create hydrogel fibers with improved resistance to water. Such cross-linked fibers with encapsulated microorganisms can be used in various applications. However, FDMA cannot be cross-linked using conventional cross-linking approaches such as exposing the fibers to a water-based cross-linking solution (Ji et al. *Biomaterials* 27(20):3782-3792 (2006)). Also, the non-volatile nature of the cross-linking agent prevents the use of vapor-phase cross-linking method (Zhang et al., *Polymer* 47(8):2911-2917 (2006); Zhong, et al. *Materials Science & Engineering C-Biomimetic and Supramolecular Systems* 27(2):262-266 (2007); and Vondran et al., *Journal of Applied Polymer Science* 109(2):968-975 (2008)). Several studies have described various other methods of creating cross-linked fibers; such as heat (Ding et al. *Journal of Polymer Science Part B-Polymer Physics* 40(13): 1261-1268 (2002); Chen et al., *Journal of Polymer Science Part a-Polymer Chemistry* 42(24):6331-6339 (2004); Li et al., *Nanotechnology* 16(12):2852-2860 (2005); Jin et al., *Macromolecular Chemistry and Physics* 206(17):1745-1751 (2005); and Li et al., *Polymer* 46(14):5133-5139 (2005) or ultraviolet (UV) radiation (Kim et al., *Macromolecules* 38(9):3719-3723 (2005); Zeng et al., *Macromolecular Rapid Communications* 26(19):1557-1562 (2005); Choi et al., *Journal of Applied Polymer Science* 101(4):2333-2337 (2006); and Ignatova et al., *Carbohydrate Research e:*2098-2107 (2006)) to initiate the cross-linking reaction during or after the synthesis of the fibers. Heat and UV light, however, have known microbicidal properties and thus are not suitable for use in this study.

It is preferable to cross-link FDMA fibers in an organic solvent to prevent its dissolution. Glycerol was chosen as the organic solvent due to its low toxicity to microorganisms. In fact, glycerol is used to preserve microorganisms at −70° C. While pure glycerol can be used, it does not lead to free-radical polymerization. In order to initiate free-radical polymerization, the fibers were exposed to a solution of glycerol and water containing a redox system consisting of ammonium persulfate (APS), ascorbic acid (AsA) and ferrous sulfate. As anticipated, the water/glycerol solution did not dissolve the electrospun fibers and allowed the subsequent cross-linking reaction to proceed. Furthermore, the low toxicity of the chosen redox system allowed the microbes to survive.

Figure 3:
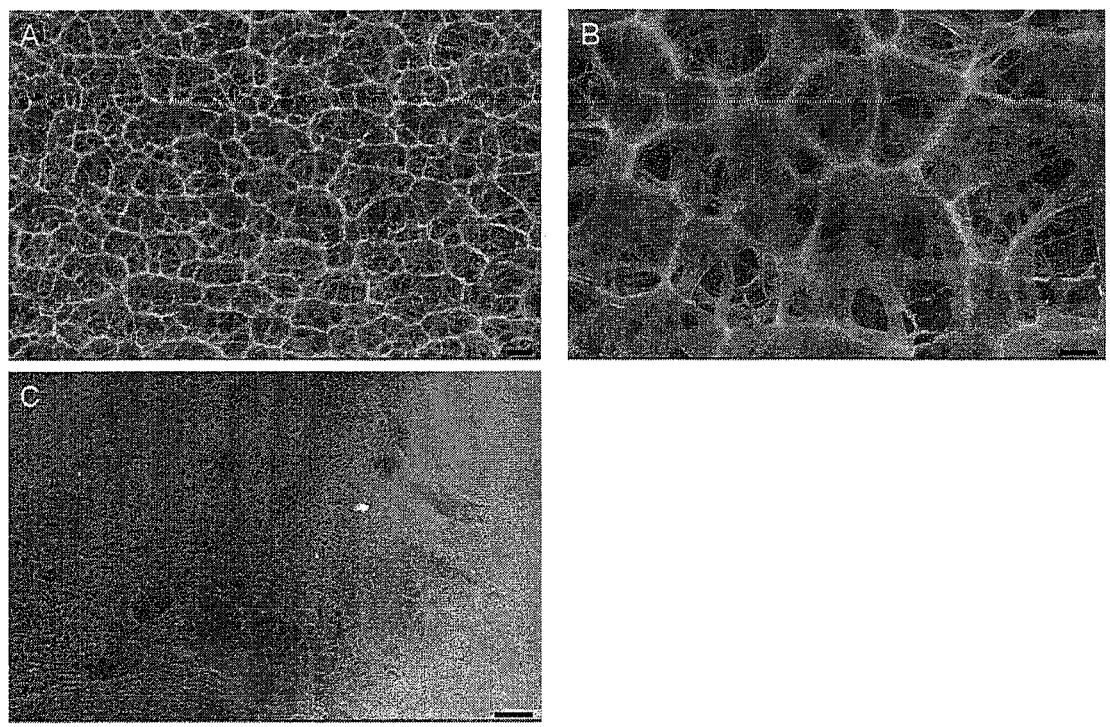
FIG. 3. (A), (B) Surface and (C) edge images of the FDMA fibrous scaffold obtained by lyophilization after PEO extraction. Bars, 20 μm (A), 10 μm (B), 100 μm (C).
Figure 4:
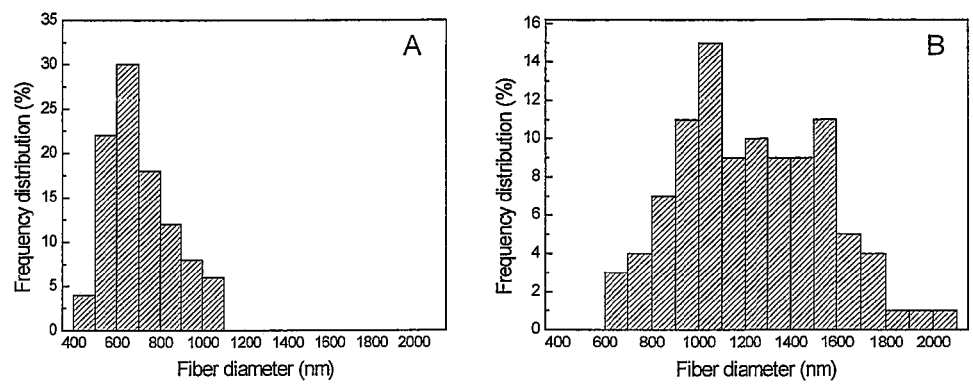
FIG. 4. Fiber diameter distribution of (A) FDMA/PEO blend fibrous scaffold electrospun from 13 wt % FDMA/PEO aqueous solution with FDMA/PEO weight ratio of 13:3 and (B) cross-linked FDMA fibrous scaffold after PEO extraction.

The as-spun FDMA/PEO blend scaffold with or without bacteria was cross-linked and subsequently soaked in deionized water to remove PEO and obtain an FDMA fibrous scaffold. The morphological change of FDMA fibrous scaffold (without bacteria) after PEO extraction is shown in FIG. 3. SEM (Scanning electron microscopy) images showed that the cross-linked FDMA scaffold still maintained the three-dimensional (3D) porous structure after PEO extraction. This structure is in agreement with the morphology of freeze-dried cross-linked fibers that were obtained via electrospinning of other polymeric materials (Ji et al., *Biomaterials* 27(20): 3782-3792 (2006)). The porous structure was not only seen on the surface of the electrospun samples (FIGS. 3A and 3B), but through the whole thickness of the sample, as apparent from FIG. 3C, which shows the cross-section (edge) of the scaffold. However, the presence of significant amount of water during cross-linking treatment had affected the fiber morphology to some extent. This was reflected by the fact that fibers at junctions were fused together forming bindings. The change in the distribution of fiber sizes before and after PEO extraction, analyzed using UTHSCSA Image Tool, are shown in FIGS. 4A and 4B, respectively. Before PEO extraction, more than 85% of fibers were within the diameter range between 500 and 900 nm. After PEO extraction, the distribution of fiber diameter became much wider and more than 74% of fibers were within the diameter range between I and 2 μm.

Figure 5:
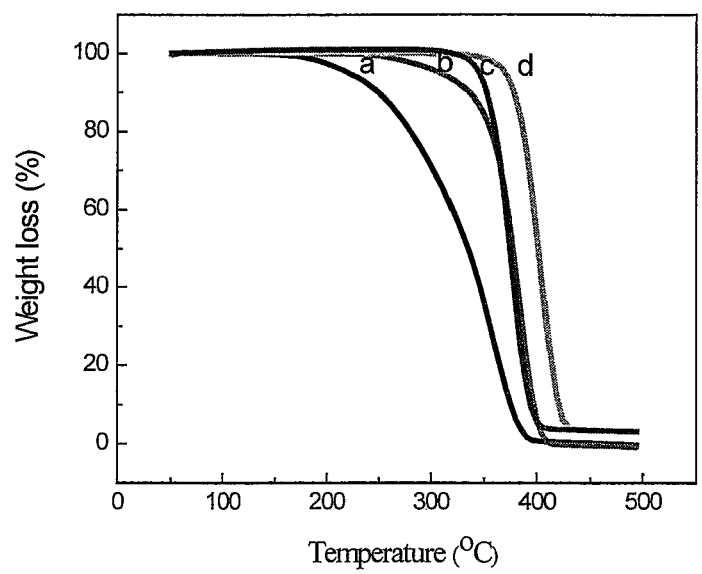
FIG. 5. TG analyses of different samples: (a) F-DMA powder, (b) F-DMA/PEO blend scaffold, (c) FDMA cross-linked scaffold and (d) PEO powder.

The TG thermograms of raw FDMA powder, the raw PEO powder, the electrospun FDMA/PEO blend scaffolds and cross-linked FDMA fibers are shown in FIG. 5. TG analysis showed that the thermal temperature of FDMA/PEO scaffolds was approximately 350° C., indicating its thermal stability in the temperature range where microorganisms are used (usually lower than 45° C.). Also, it should be noted that the thermal degradation temperature of the FDMA/PEO blend was between the thermal degradation temperature of pure PEO powder and FDMA powder, suggesting the mixture of PEO and FDMA in the electrospun blend scaffold. On the other hand, TG analysis showed that the thermal degradation temperature of cross-linked FDMA scaffolds increased from 200° C. to 350° C. The increase of the degradation temperature can be readily attributed to the presence of inter-chain molecular cross-links.

Figure 6:
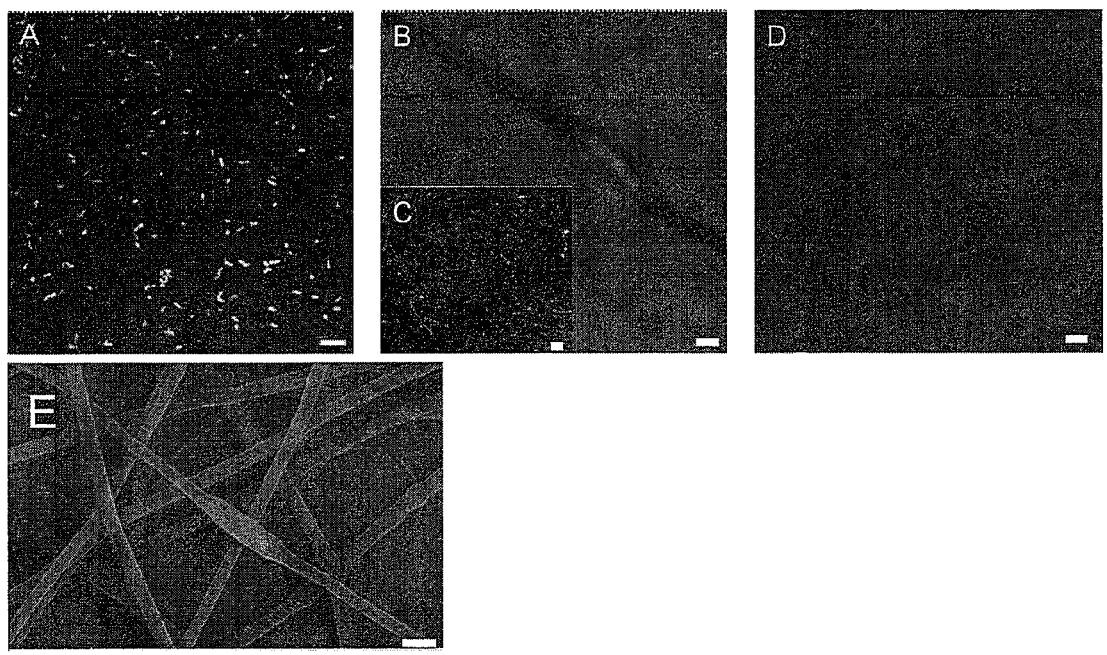
FIG. 6. Confocal images of stained and fluorescent *P. fluorescens* cells (the red and green spots) (A) before electrospinning. (B) and (C) show the morphology of the bacteria inside the dry electrospun FDMA/PEO blend fibers. (0) Image of stained and fluorescent *Z. mobilis* cells in dry electrospun FDMA/PEO blend fibers. SEM micrographs of uranyl acetate stained *P. fluorescens* cells after electrospinning (E). Bars, 10 μg/m (A), 1 μm (B), 20 μm (C), 2 μm (D), and 1 μm (E).

The above method was then used to encapsulate rod-shaped bacteria in a polymer matrix, which forms a composite fiber during electrospinning. The bacteria were initially suspended in the FDMA/PEO aqueous solution, in which they were found to be randomly oriented (FIG. 6A). After electrospinning, the rod-like bacteria were found to be oriented, mainly along the direction of the fibers (FIGS. 6B & C). Lower magnification image (FIG. 6C) showed that the microbes were distributed over the entire area of the electrospun fibers. With higher magnification using confocal microscopy, the individual bacterium could be discerned within these fibers. FIG. 6D shows a representative cell of the *P. fluorescens* bacterium inside the electrospun FDMA/PEO fibers. The microorganisms were found to be fully encapsulated by the fibers and oriented in the longitudinal direction of the fiber. Similar morphology was also observed when *Z. mobilis* was encapsulated in the electrospun fiber as shown in FIG. 6E. In all these circumstances, the fiber diameter were found to be only slightly larger than the average size of the microbes used, thereby encapsulating the bacterium with only a thin layer of the polymeric material.

To obtain higher magnification images and to confirm the cellular integrity of bacteria within the single fiber, SEM microscopy was required. To this extent, uranyl acetate was used as a contrast agent to differentiate the microbe from the polymer. FIG. 6E presents SEM images of uranyl acetate stained *P. fluorescens* prior to and after electrospinning. FIG. 6E clearly shows that the polymeric matrix has fully encapsulated the bacterial cell causing a local widening of the fiber. This image further confirms that, during the electrospinning process, the bacteria were oriented in the direction of the fibers.

Figure 12:
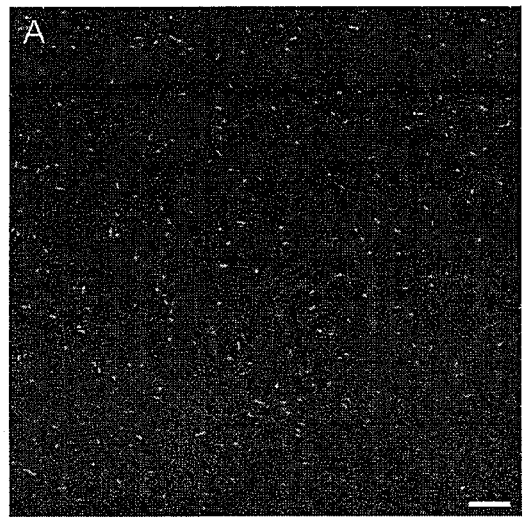
FIG. 12: Confocal images of GFP-E. coli (A) before and (B) after electrospinning. The fluorescence property of GFP-E. coli makes cells encapsulated in the electrospun F127 DMA/PEO fibers visible. Bars, 20 μm.
Figure 12:
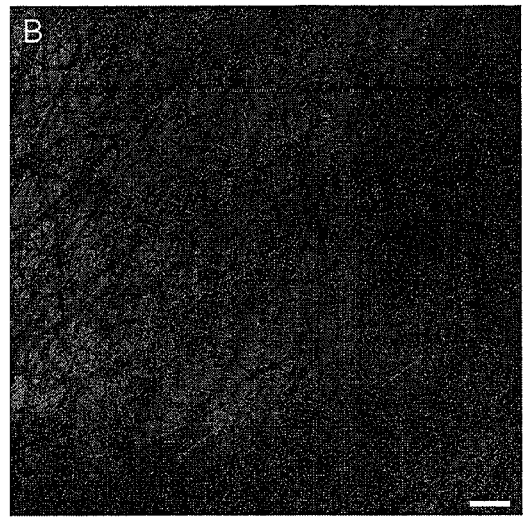

Furthermore, GFP *E. coli* were also encapsulated using this process and examined using confocal microscopy. While, the innate fluorescence of GFP *E. coli* was used to easily image the encapsulated bacteria under confocal microscopy images, the intensity of the fluorescence was weaker than those obtained from bacterial cells before electrospinning (FIG. 12). This is only expected as the intensity of fluorescence is decreased by the polymeric capsule around the bacterial cell. Encapsulation of *E. coli* shows the broad applicability of this process.

Figure 7:
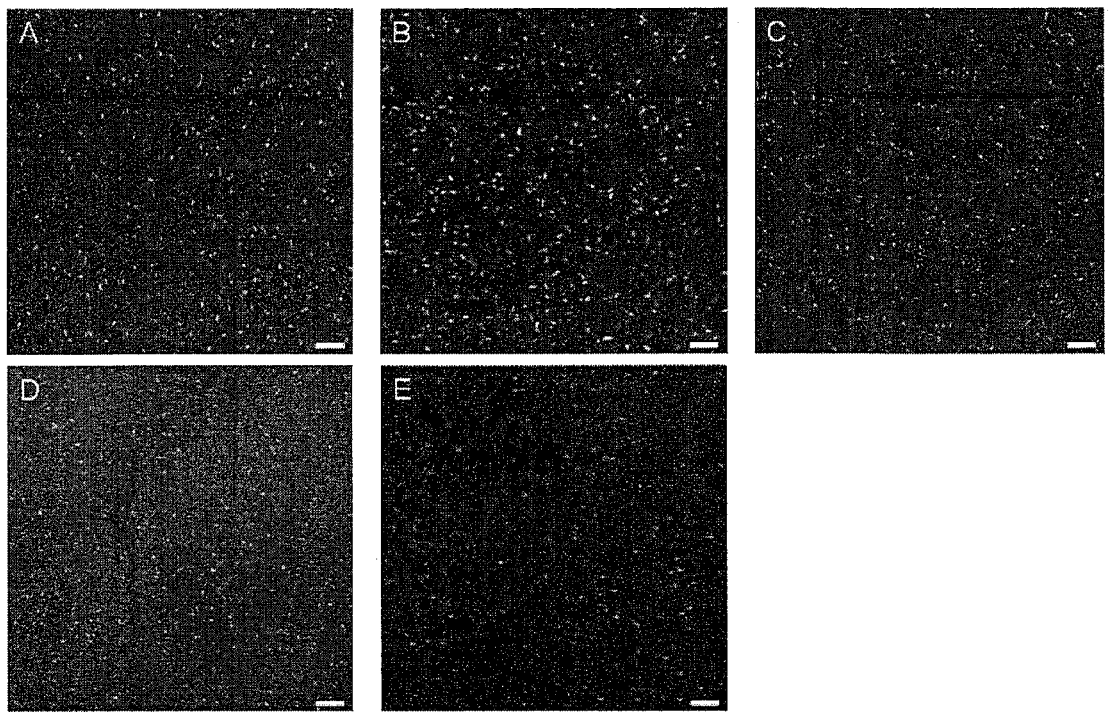
FIG. 7. Confocal images of Z. mobilis cells (A) before electrospinning; (B) immediately after electrospinning; and after storage at 4° C. under saturated humidity, with the exclusion of light for (C) 1 day; (0) 3 days; and (E) 7 days. Bars, 20 μm.
Figure 13:
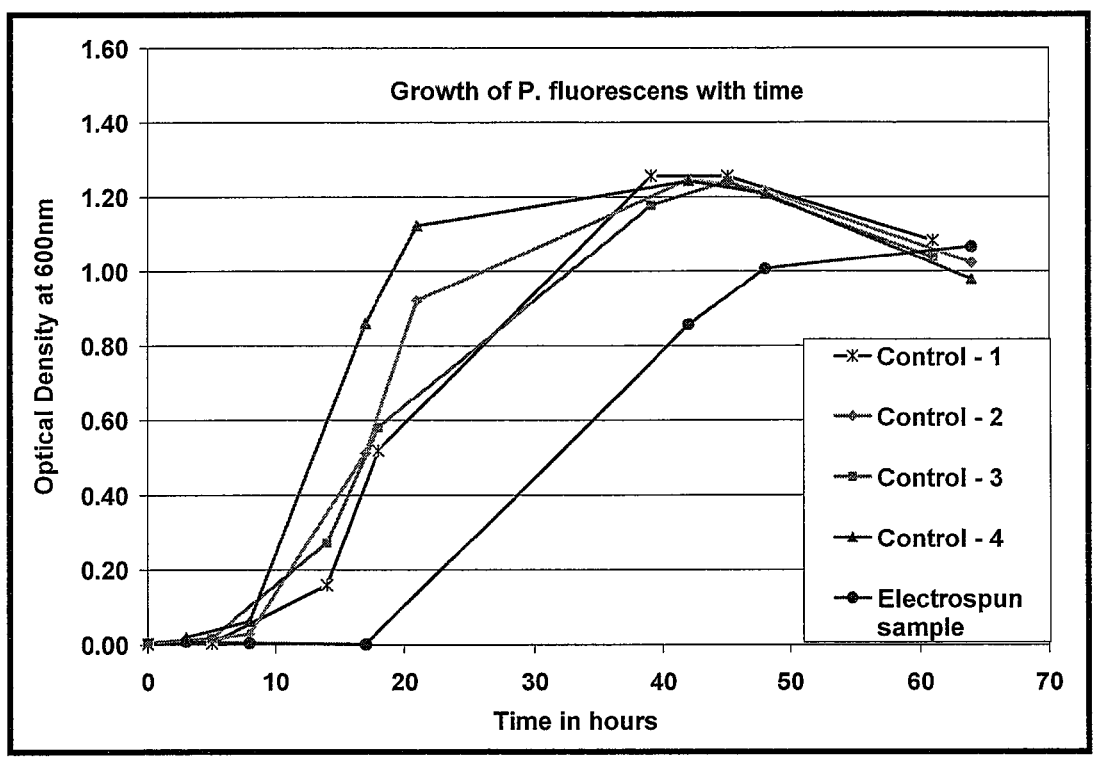
FIG. 13: The growth of electrospun-immobilized and free P. fluorescens in an Erlenmeyer flask containing 50 ml of sterile growth media as monitored by absorption at 600 nm against a culture medium blank. Controls, 1, 2 and 3 are from inoculation of 50, 100 and 250 μl of a fresh culture. Control 4 and Electrospun samples denote the growth observed when inoculated with 100 μl of polymer solution containing the bacteria just prior to and immediately after electrospinning.
Figure 14:
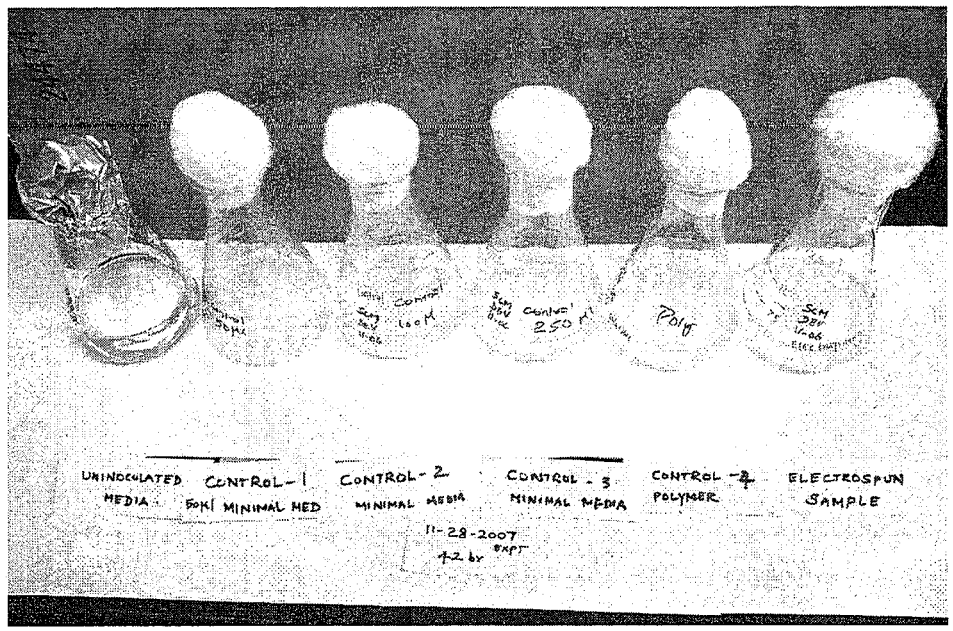
FIG. 14: A photo of the un-inoculated culture medium and the five inoculated flasks showing the growth of P. fluorescens after 42 hours of growth (data shown in previous FIG. 13). Controls 1, 2 and 3 are from inoculation of 50, 100 and 250 μl of a fresh culture. Control 4 and Electrospun sample denote flasks inoculated with 100 μl of polymer solution containing the bacteria just prior to and immediately after electrospinning.

It was found that exposure to FDMA and PEO had little or no effect on the viability of the bacteria, even when the bacteria were maintained in this solution for up to a week before assaying them. As described above, electrospinning is an efficient method to encapsulate bacteria in the polymer fiber. However, in the electrospinning process, the removal of water by rapid evaporation is anticipated to cause drastic changes in the osmotic environment of the organism (Gensheimer et al., *Advanced Materials* 19(18):480). Even more, an electric field is generated by applying a high voltage between the metal capillary and the collector, which may be harmful to the bacteria. In the present study, *Z. mobilis* suspended in a polymeric solution were electrospun, stained with bacterial viability kits, and examined immediately after electrospinning. The images obtained before and after electrospinning are shown in FIGS. 7A-E. FIG. 7B showed that most (about 93%) of the bacteria were viable immediately after the electrospinning process (viewed as green in the images), before conducting the cross-linking and PEO extraction steps. When these electrospun fibers were dissolved in culture medium, the bacteria were released from the fibers and their growth was monitored at 600 nm (FIGS. 13 and 14). It was seen that while the electrospun microorganisms had a slightly longer lag-phase of growth, their growth was barely affected by electrospinning.

The effect of storage on the viability of encapsulated bacteria is an important issue for their potential deployment in industrial-scale processes, since the application of these novel bioactive materials requires the bio-hybrid system to be intact and functional (microorganism to be viable) at the time of use at a desired site (Salalha et al., *Nanotechnology* 17(18): 4675-4681 (2006)). To test the viability of the microbes in the fiber over time, the bacteria-containing scaffolds were maintained under saturated humidity conditions and under exclusion of light at 4° C., for up to 7 days. After 1, 3 and 7 days, bacteria encapsulated FDMA/PEO fiber were dissolved in the deionized water to liberate the bacteria. It was determined that although the viability of bacteria decreased over time, significant amount of the bacteria remained viable: ~62%, 47% and 23% were found to be viable after 1 day (FIG. 7C), 3 days (FIG. 7D), and 7 days (FIG. 7E), respectively. Further, to test whether the functionality (metabolic pathway) of the microbe was affected, the uncross-linked fibers containing encapsulated microbes were suspended in growth media and the metabolic produces were assessed. *Z. mobilis* is well known for its ethanologenic activity and thus the amount ethanol produced (vol %) was assessed. The results showed that the metabolic activity of the microorganism was not affected by the electrospinning process, and the amount of ethanol produced by the encapsulated microbes was found to be in good agreement with the amount produced by un-encapsulated (free culture) control (FIG. 16). This was found to be the case after one week of storage at −4° C. and up to two months of storage at −70° C. It is thus apparent that the electrospinning process does not adversely affect the metabolic pathway of the microbes.

Although the cross-linking treatment improved the water-resistance and thermal properties of the electrospun FDMA fibrous membranes, an eventual adverse effect is that such treatment could be cytotoxic to bacteria encapsulated in the fiber. The cytocompatibility of the cross-linking step is critical to the ultimate success of this study. Although polymerization of monomers with carbon-carbon double bonds has been extensively investigated in the past using photopolymerization/photo-crosslinking, this method cannot be used for the preparation of cross-linked FDMA fibers encapsulated with bacteria. This is not only because the UV light has known microbicidal properties, but also because photopolymerization cannot be carried out uniformly in a large or thick system. Furthermore, the light penetration depth is quite limited and light distribution is inhomogeneous. Chemical cross-linking seems to be a more suitable method for the purpose of this study, although it could be potentially toxic when the bacteria encapsulated in the electrospun fibers are exposed to the cross-linking agent. The most commonly used free radical initiator consists of N,N,N',N'-tetramethylethylenediamine (TEMED) and peroxodisulfate (potassium or ammonium salt). The function of TEMED is to accelerate the homolytic scission of the peroxodisulfate anion yielding the TEMED free radical, which initiates the polymerization of the methacrylate groups. TEMED, due to its high efficiency, is the most widely used free-radical polymerization catalyst. However, TEMED has been observed to be toxic to microbes.

Previous literature has also reported that FDMA could be cross-linked by free radical polymerization at 37° C. using a redox system which included APS (Ammonium persulfate) and sodium metabisulfite. However, sodium metabisulfite releases sulfur dioxide ($SO_2$) when exposed to water. To prevent any interference from gas evolution and possible changes in the pH due to $SO_2$ on the cross-linking reaction, the system comprising of ferrous sulfate and AsA was used instead of sodium metabisulfite. Ferrous sulfate is a component of several bacterial growth media and unlike metabisulfite does not degrade in water. The concentration of the APS, ferrous sulfate and AsA was adjusted to as low as possible, by iterative experimentation, to minimize the oxidation of microbes by APS.

Figure 8:
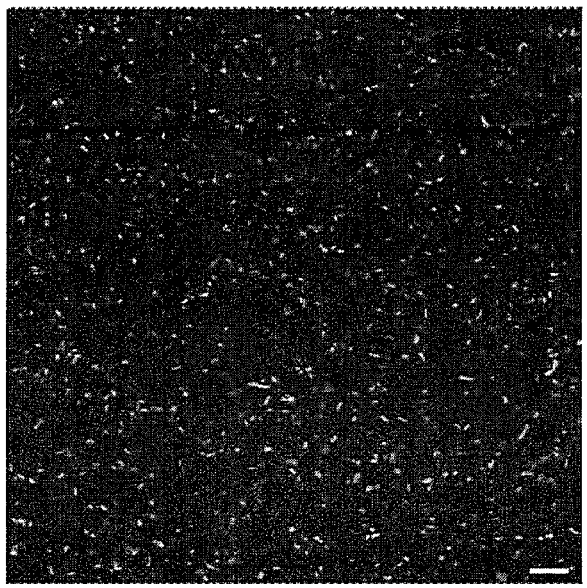
FIG. 8. The confocal microscopy of Z. mobilis within the cross-linked FDMA fibers shows that about 40% of the bacteria were still alive after the electrospinning and cross-linking process. Before the imaging, the fibers encapsulated with bacteria were cross-linked, rinsed with DI water and stained with LIVE/DEAD® BacLight™ bacterial viability kits. Note that the cross-linked FDMA fibers were still wet when the picture was taken. Bar, 10 μm.

The *Z. mobilis* encapsulated FDMA cross-linked fibers were washed with deionized water three times and stained with LIVE/DEAD® BacLight™ bacterial viability kits to visualize the bacteria under the confocal microscope. The confocal microscopy image shown in FIG. 8 revealed that about 40% of the bacteria were still alive after the electrospinning and cross-linking process.

Figure 9:
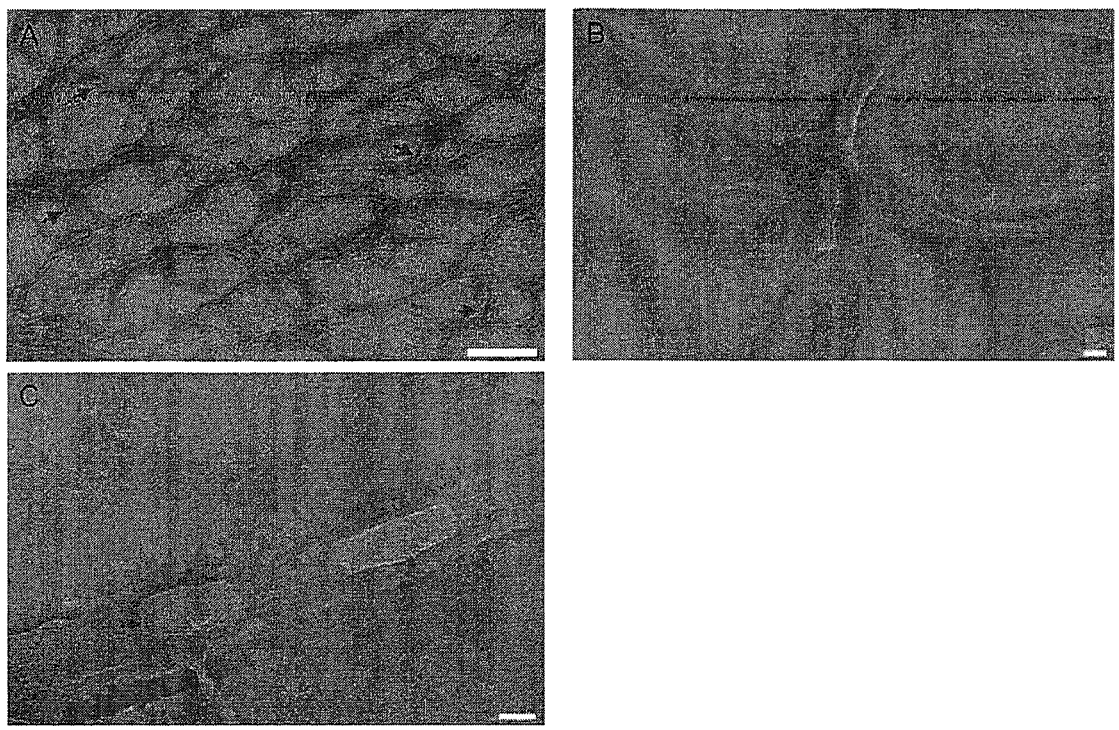
FIG. 9. SEM images of Z. mobilis in the cross-linked FDMA fibers. Normally, the cross-linked FDMA fibers are multi-layered. Mono-layer of Z. mobilis cells encapsulated FDMA fibers is shown here, because it provides better contrast between the microorganism and fiber. Arrows in image (A) indicate the position of the bacteria. Magnification is indicated individually on data bar at the bottom of micrograph. Bars, 10 μm (A), 1 μg/m (B, C).

To verify encapsulation of *Z. mobilis* cells by the FDMA fiber, freeze-dried cross-linked FDMA fibers encapsulating the bacteria were examined. FIG. 9A shows a homogeneous distribution of bacteria in the cross-linked material. Microbes were found to be encapsulated both at the junctions where fibers fused together (FIG. 9B) as well as in single fiber (FIG. 9C), with the cellular integrity of the microorganism appearing to be well preserved, regardless of the location.

Figure 10:
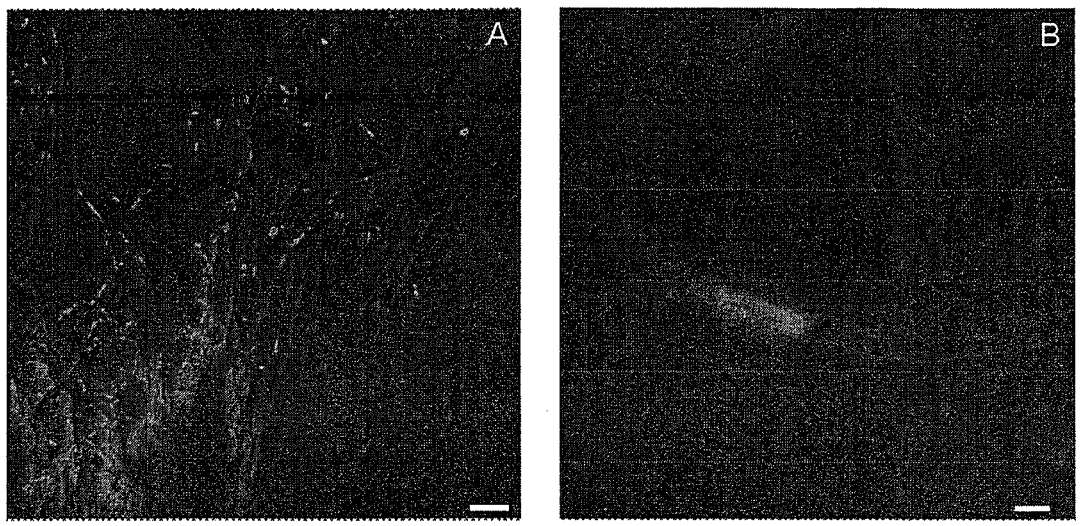
FIG. 10. Confocal microscopic images of GFP-E. coli on wet cross-linked FDMA fibers. The fibers encapsulated with GFP-E. coli was cross-linked and rinsed with deionized water, and imaged under the confocal microscope immediately. Bars, 10 μm (A), 1 μm (B).
Figure 11:
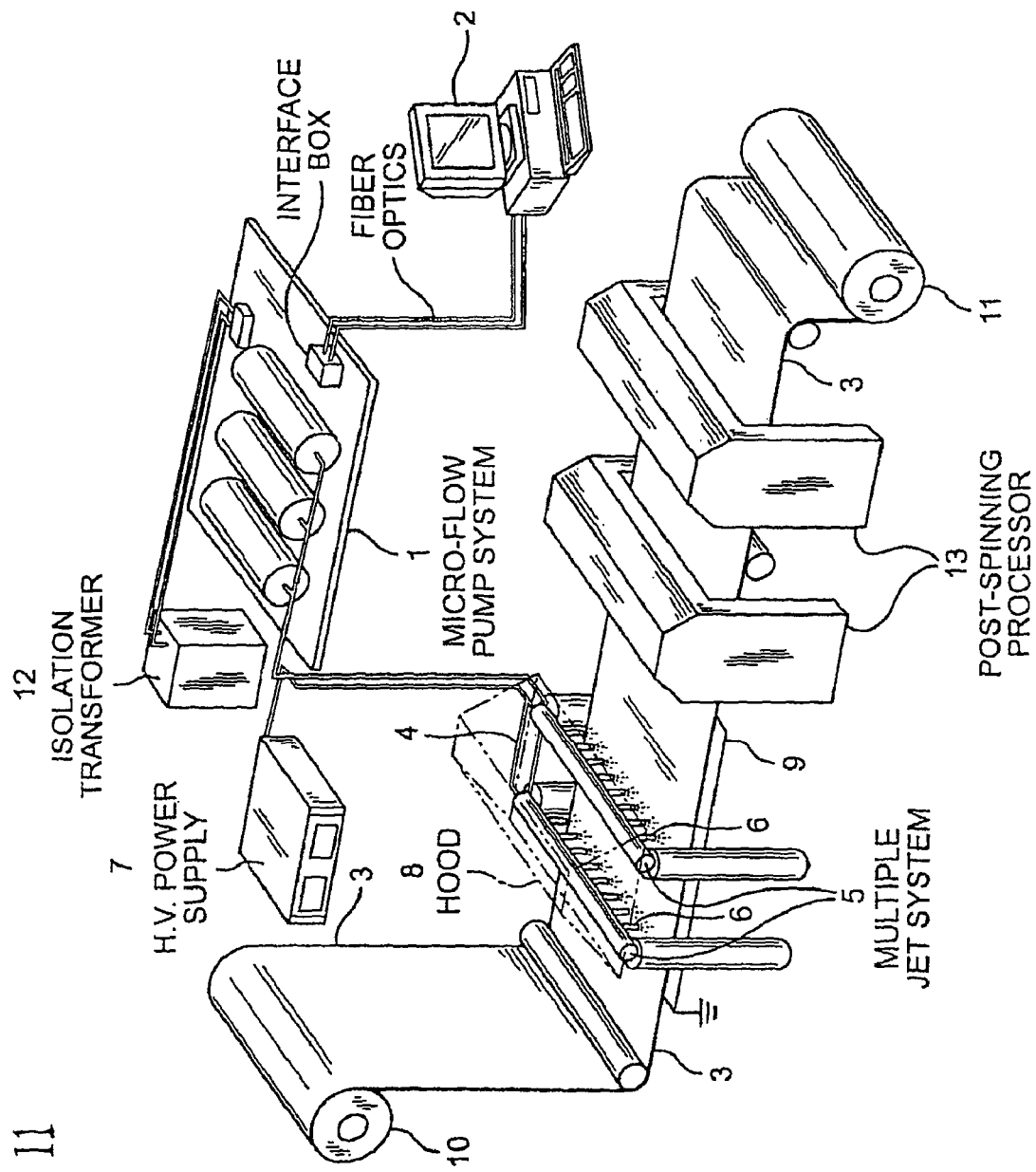
FIG. 11 is a schematic of an electrospinning system.

By means of confocal microscopy, *E. coli* could be detected immediately after cross-linking inside the fibers. To confirm the presence of the *E. coli* within the cross-linked fibers, it was necessary to study a monolayer of fibers as deposited on a silicon wafer. Thus, the edges of the cross-linked hydrogel scaffold deposited on silicon, which tend to have fewer layers and therefore are thinner than the center, were studied under confocal microscope as shown in FIG. 10A. The image of *E. coli* in cross-linked fibers (FIG. 10A) was brighter than in the dry blend FDMA/PEO fibers (FIG. 12). This may be due to the swelling of the cross-linked fibers in the deionized water and the formation of the hydrogel material, as well as the removal of the high molecular weight PEO via extraction in water. With higher magnification, single bacterium within the cross-linked fibers could be observed. FIG. 10B shows that the *E. coli* to be oriented in the longitudinal direction of the fiber, with no morphological changes being observed due to the cross-linking reaction.

The invention claimed is:

1. A porous film comprising crosslinked electrospun hydrogel fibers, wherein microbes are encapsulated within the crosslinked electrospun hydrogel fibers, and wherein the crosslinked electrospun hydrogel fibers are water insoluble and permeable, and contain viable microbes encapsulated within the fiber.

2. The porous film of claim 1 wherein the film has an open pore structure.

3. The porous film of claim 1 wherein the crosslinked electrospun hydrogel fibers comprise polyethers.

4. The porous film of claim 3 wherein the polyethers comprise polyethylene oxide, polypropylene oxide, mixtures thereof, or co-polymers thereof.

5. The porous film of claim 4 wherein the copolymer is a triblock copolymer of polyethylene oxide-polypropylene oxide-polyethylene oxide.

6. The porous film of claim 5 wherein the polyethers comprise a mixture of the triblock copolymer and polyethylene oxide.

7. The porous film of claim 3, wherein the polyethers are functionalized with terminal acrylate or methacrylate groups.

8. The porous film of claim 1 wherein the crosslinked electrospun hydrogel fibers comprise a mixture of $PEO_{99}$-$PPO_{67}$-$PEO_{99}$ DMA and polyethylene oxide.

9. The porous film of claim 1 wherein the crosslinked electrospun hydrogel fibers comprise glycosaminoglycans.

10. The porous film of claim 9 wherein the glycosaminoglycans comprise functionalized hyaluronic acid.

11. The porous film of claim 1 wherein the crosslinked electrospun hydrogel fibers comprise proteins.

12. The porous film of claim 1 wherein the microbes are capable of bioremediation.

13. The porous film of claim 12 wherein the microbes are *Pseudomonas* sp.

14. The porous film of claim 1 wherein the microbes produce ethanol.

15. The porous film of claim 14 wherein the microbes are *Zymomonas* sp.

16. The porous film of claim 1 wherein the microbes maintain viability for at least about one week at 4° C.

17. The porous film of claim 1, wherein the crosslinked electrospun hydrogel fibers have diameters in the range of about 0.6 microns to about 5 microns.

18. The porous film of claim 1, wherein the porous film has a thickness in the range of about 1 micron to about 10 cm.

19. The porous film of claim 18, wherein the porous film has a thickness in the range of about 10 to about 5000 microns.

20. A method of encapsulating microbes within crosslinked electrospun hydrogel fibers, the method comprising:
   (a) providing a mixture of microbes and a polymer, wherein the polymer is water soluble, is crosslinkable, and is capable of forming a hydrogel upon being crosslinked;
   (b) electrospinning the polymer to form electrospun fibers, wherein microbes are encapsulated within the electrospun fibers; and
   (c) crosslinking the electrospun fibers to form crosslinked electrospun hydrogel fibers,
   wherein the crosslinked electrospun hydrogel fibers are water insoluble; and
   wherein viable microbes are encapsulated within the fiber of the crosslinked electrospun hydrogel fibers.

21. The method of claim 20 wherein the electrospun hydrogel fibers are crosslinked by contacting the electrospun hydrogel fibers with a crosslinking agent in a liquid polyol.

22. The method of claim 21 wherein the liquid polyol is glycerol.

23. The method of claim 21 wherein the liquid polyol is a sugar alcohol.

24. The method of claim 23 wherein the sugar alcohol is xylitol, mannitol or lactitol.

25. The method of claim 21 wherein up to about 70% of the liquid polyol is replaced with water.

26. The method of claim 21 wherein up to about 50% of the liquid polyol is replaced with water.

27. The method of claim 21 wherein up to about 30% of the liquid polyol is replaced with water.

28. The method of claim 20 wherein the electrospun hydrogel fibers are crosslinked by contacting the electrospun hydrogel fibers with redox system that produces a free radical inhibitor in a solvent that comprises a liquid polyol and optionally water.

29. The method of claim 28 wherein the redox system comprises at least a persulfate salt.

30. The method of claim 29 wherein the persulfate salt is ammonium persulfate.

31. The method of claim 28 wherein the redox system comprises ammonium persulfate, ferrous sulfate and ascorbic acid.

32. A method of crosslinking electrospun fibers in which microbes are encapsulated, the method comprising crosslinking in a liquid polyol; wherein, after crosslinking, (i) the electrospun fibers form crosslinked electrospun hydrogel fibers that are insoluble and permeable, and (ii) wherein viable microbes are encapsulated within the fiber of the crosslinked electrospun hydrogel fibers.

33. The method of claim 32 wherein the act of crosslinking comprises treating the electrospun fibers with ammonium persulfate, ferrous sulfate and ascorbic acid.

34. The method of claim 32 wherein the liquid polyol is glycerol.

35. The method of claim 32 wherein up to about 70% of the liquid polyol is replaced with water.

36. A biosensor comprising microbes encapsulated within crosslinked electrospun hydrogel fibers, wherein the microbes are viable and capable of generating a signal in response to a chemical compound; and wherein the crosslinked electrospun hydrogel fibers are water insoluble and permeable, and contain viable microbes encapsulated within the fiber of the crosslinked electrospun hydrogel fibers.

37. The biosensor of claim 36 wherein the signal is an electric signal.

38. An electrode comprising crosslinked electrospun hydrogel fibers, wherein microbes are encapsulated within, and wherein the crosslinked electrospun hydrogel fibers, are water insoluble and permeable, and contain viable microbes encapsulated within the fiber of the crosslinked electrospun hydrogel fibers, and are capable of electron generation or utilization.

39. The porous film of claim 1 wherein the porous film is used in a bio-film reactor and wherein the encapsulated microbes are further capable of producing metabolites.

* * * * *